US008323245B2

(12) United States Patent
List et al.

(10) Patent No.: US 8,323,245 B2
(45) Date of Patent: Dec. 4, 2012

(54) INFUSION DEVICE AND METHOD

(75) Inventors: Hans List, Hesseneck-Kailbach (DE);
Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 245 days.

(21) Appl. No.: 12/362,795

(22) Filed: Jan. 30, 2009

(65) Prior Publication Data
US 2009/0192461 A1    Jul. 30, 2009

(30) Foreign Application Priority Data

Jan. 30, 2008    (EP) .................................... 08001688

(51) Int. Cl.
*A61M 37/00*    (2006.01)
*F04B 49/00*    (2006.01)
(52) U.S. Cl. ........................................ 604/131; 417/214
(58) Field of Classification Search .................. 604/151, 604/152, 154; 368/129; 417/214, 326; 74/814
See application file for complete search history.

(56) References Cited

U.S. PATENT DOCUMENTS

| 3,685,371 | A | * | 8/1972 | Crooks ........................ 475/299 |
| 4,676,122 | A | * | 6/1987 | Szabo et al. ................... 74/625 |
| 4,828,551 | A | | 5/1989 | Gertler et al. |
| 4,868,801 | A | * | 9/1989 | Dold ............................ 368/139 |
| 5,006,112 | A | | 4/1991 | Metzner |
| 5,176,646 | A | * | 1/1993 | Kuroda ........................ 604/154 |
| 2002/0071225 | A1 | | 6/2002 | Sheldon et al. |
| 2005/0238507 | A1 | | 10/2005 | Dilanni et al. |
| 2006/0184121 | A1 | * | 8/2006 | Brockman et al. ............ 604/151 |
| 2006/0184124 | A1 | * | 8/2006 | Cowan et al. ................. 604/155 |

FOREIGN PATENT DOCUMENTS

| EP | 0369322 A2 | 5/1990 |
| GB | 2308067 A | 6/1997 |
| WO | 02/068015 A2 | 9/2002 |
| WO | 2006/078817 A2 | 7/2006 |

* cited by examiner

*Primary Examiner* — Nicholas Lucchesi
*Assistant Examiner* — Jenna Zhang
(74) *Attorney, Agent, or Firm* — Bose McKinney & Evans LLP

(57) ABSTRACT

An infusion device with safeguards for protecting a patient from inappropriate infusion during a malfunction comprises a pump, an electronic controller for controlling the pump, and a mechanical stop facility for stopping the pump by mechanically blocking pump motion. The stop facility periodically requires resetting by the controller to continue infusion.

14 Claims, 2 Drawing Sheets

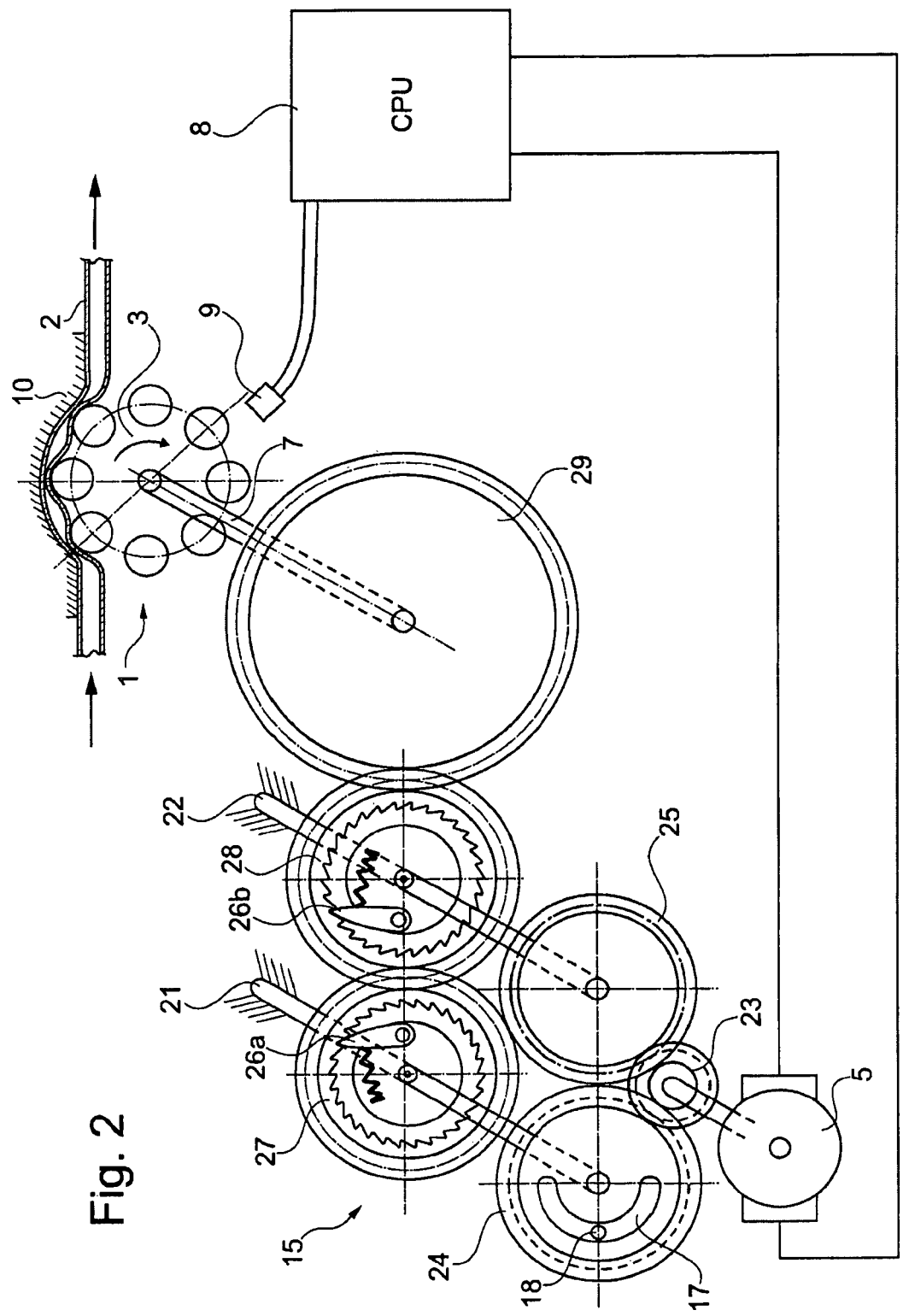

INFUSION DEVICE AND METHOD

REFERENCE

This application claims priority to European Patent Application No. EP 08 001 688.4 filed Jan. 30, 2008, which is hereby incorporated by reference.

FIELD

The invention refers to an infusion device comprising a pump and an electronic controller for controlling the pump. Such infusion devices are used to deliver insulin or other medication to a patient.

BACKGROUND

The accuracy of medication delivery is critical, since minor differences in medication quantity can dramatically affect the health of a patient. Thus, safeguards must be designed into the delivery system to protect the patient from over or under delivery of medication. For example, in the case where insulin is administered via an infusion device to a diabetic patient, excessive insulin delivery could cause complications due to hypoglycaemia, and possibly even result in death. Therefore, controlled delivery with safeguards against over delivery of medications is required for infusion devices.

Safeguards against over delivery have been incorporated into electronic controllers of infusion pumps in varying ways. For example, the controller may comprise a microprocessor that monitors motor current consumption to detect a malfunction or utilize sensors for occlusion detection or the like. However, a malfunction of the controller itself, for example a direct short from the power source to the pump motor, might cause the pump motor to drive continuously and deliver all the medication contained in the infusion system over a short period and thereby cause severe over delivery.

To guard against such a malfunction US 2002/0071225 A1 teaches to provide infusion devices with a safety circuit system that this designed to cause a disconnection of a drive motor of the pump when the controller fails.

To increase the operational safety of infusion devices it is also known to use solenoid actuators or stepper motors to drive the infusion pump. Although in this way the risk of a continued infusion in case of a controller failure may be significantly reduced, solenoid actuators or stepper motors are rather expensive and not nearly as energy efficient as DC motors. Large energy consumption is a serious disadvantage as larger and heavier batteries are required which is incompatible with the standard design objective to make infusion devices small, compact and light-weight.

SUMMARY

It is therefore an object of embodiments of the invention to provide a cost and energy efficient way to improve the safety of ambulatory infusion devices.

An infusion device according embodiments of the invention has a mechanical stop facility for stopping the pump by mechanically blocking pump motion. Such a mechanical stop facility can be used to reliably stop an infusion even if the pump motor is still powered due to a failure of the electronic controller. The stop facility can block pump motion by positive locking, although friction locking may also be used. An especially simple and yet reliable way of stopping an infusion is a stop facility that stops the pump by mechanically locking a driveshaft, e.g. by means of a locking plate.

Significantly increased safety may be achieved if the stop facility is configured such that it periodically requires resetting by the controller to continue an infusion. For example, resetting of the mechanical stop facility may comprise moving a locking member out of an engagement position. Another possibility is a stop facility that comprises a reversing transmission and two limit stops which periodically require a reversing of rotation. Such a stop facility may be reset by reversing the direction of rotation of the reversing transmission.

A stop facility that periodically requires resetting by the controller to continue an infusion ensures that in the case of a failure of the controller pump motion is blocked after a rather short time as a faulty controller will fail to reset the stop facility. Therefore, over dosing is limited to the amount that can be infused in the time period between resets, i.e. the time between the last reset and the stopping action of the stop facility when the required reset does not occur.

It is possible to configure the stop facility in such a way that it has to be reset in fixed time intervals, which may be anything from a few seconds to several minutes. The stop facility can also be configured in such a way that it has to be reset after a drive shaft or other rotating part of the pump has rotated by a predetermined angle of rotation, for example a half turn or a full turn. Periodically resetting refers in such a device to a rotation period or any fraction thereof which depending on current infusion rates may take a variable length of time. For example, the stop facility may block pump motion by engaging a rotating mechanical element, e.g. a protrusion or a recess, for positive locking. The stop facility can comprise a spring biased locking member. The spring forces the locking member into a positive locking engagement with a suitable counterpart, a recess for example. The counterpart may be fixed to the drive shaft or some other rotating part of the pump. For resetting the stop facility, the locking member has to disengage which may be done by an actuator, e.g. a solenoid, controlled by the electronic controller.

In some embodiments, the stop facility comprises at least two locking members which alternately block pump motion. Resetting the stop facility may then be done by moving one of the locking members to disengage from locking engagement which activates at least one other locking member so that it will block pump motion after a preset period. For example, an actuator may be used for resetting locking elements in such a way that the actuator, e.g. a winding core, moves between two positions and thereby always pushes either one of two locking members away from a rotating mechanical locking element like a locking plate. Hence, by moving one locking member to disengage from a locking engagement the other locking member is no longer pushed away from the locking element and may engage it as soon as it has rotated far enough. The locking members may be spring biased to readily engage the locking element.

The pump can be a peristaltic pump. Peristaltic pumps enable a precise dosing even at very low infusion rates. Especially well suited is a rotary peristaltic pump, although other pumps may also be used. Preferably the peristaltic pump comprises a rotor with at least four, preferably at least five, annularly arranged compressing elements for acting in peristaltic fashion on a flexible tube conveying a liquid to be infused. Then, at least one of the uniformly distributed compressing elements will always reliably compress the tube and thereby close it. Hence, whenever the pump is stopped, no liquid flow can occur.

The pump motor can be a DC motor as such motors are efficient and inexpensive although other motors may also be used.

The stop facility can cause disconnection of the motor if it is not reset within a preset time. For example the stop facility may upon blocking pumping motion actuate a time delayed switch which will disconnect the motor if no corrective action is taken by the controller within the preset time.

BRIEF DESCRIPTION OF THE DRAWINGS

Further details and advantages of embodiments of the invention are illustrated in the following by means of exemplary embodiments and by making reference to the appended drawings. Identical and corresponding parts of the embodiments are denoted by the same reference numbers. In the figures.

DETAILED DESCRIPTION

Figure 1:
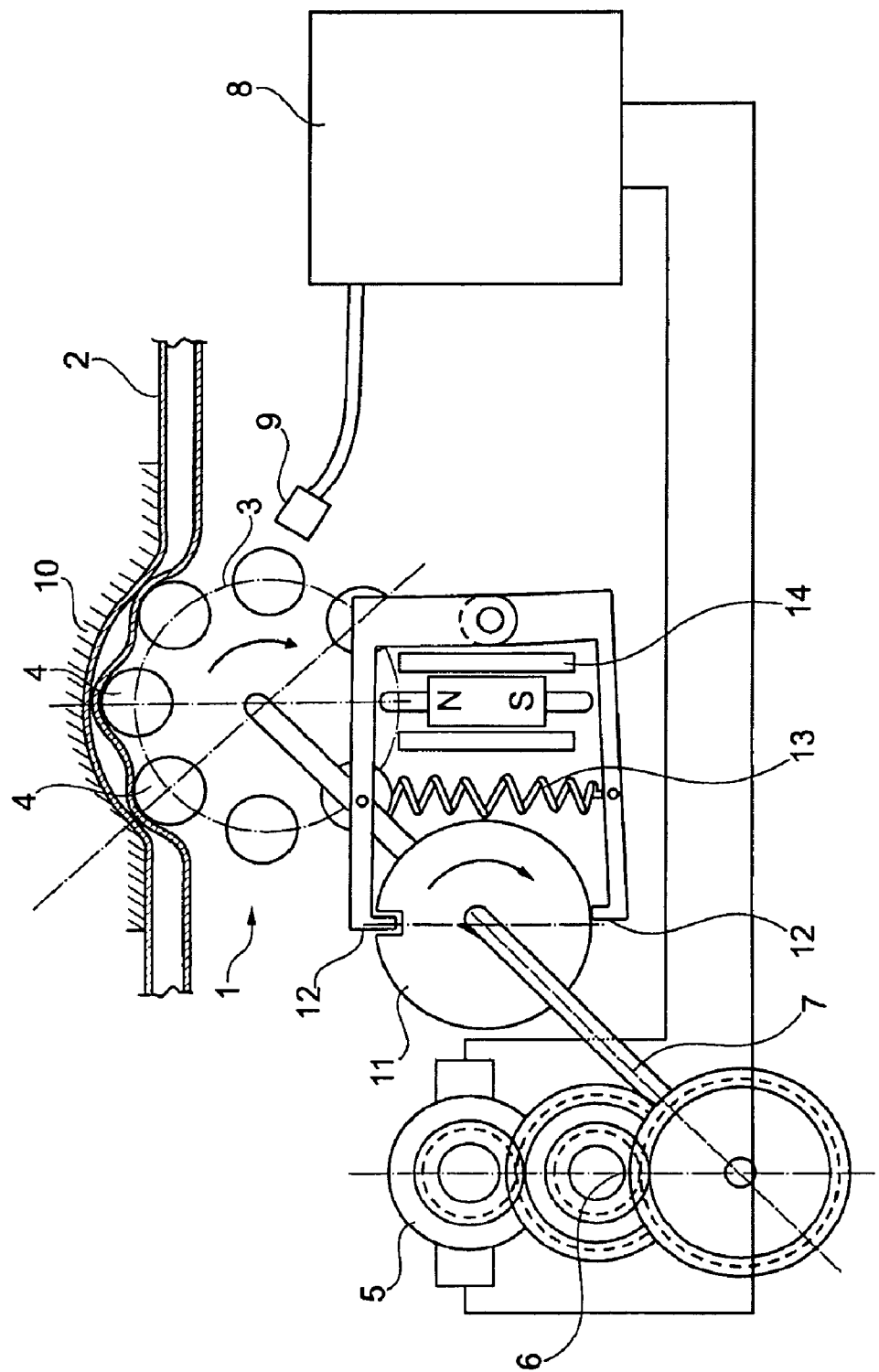
FIG. 1 shows schematically an exemplary embodiment of an infusion device according to the invention; and, FIG. 2 shows schematically a second exemplary embodiment of an infusion device according to the invention.

FIG. 1 shows schematically an embodiment of an infusion device. The infusion device comprises a peristaltic pump 1 acting on a flexible tube 2 to pump a liquid to be infused, for example insulin. The peristaltic pump 1 has a rotor 3 with more than four compressing elements 4, and in some embodiments more than five compressing elements 4, which act in peristaltic fashion on the flexible tube 2 supported by an arcuate pump bed 10. Stopping the rotor 3 blocks liquid flowing through to the tube 2 as there is always at least one compressing element 4 pressing on the tube 2 and thereby closing it. In the example shown the rotor 3 of the peristaltic pump 1 has eight compressing elements 4.

The rotor 3 of the peristaltic pump 1 is driven by a DC-Motor 5 via a transmission 6 and a drive shaft 7. The DC motor 5 is controlled by an electronic controller 8, for example a microprocessor, that monitors by means of a sensor 9 rotation of the rotor 3 and thereby the infusion rate.

The infusion device shown in FIG. 1 comprises a mechanical stop facility for stopping the pump 1 by mechanically blocking pump motion. The stop facility comprises a locking plate 11, which is connected to the drive shaft 7, and a locking member 12 which interacts with the locking plate 11. In order to lock the drive shaft 7 the locking member 12 engages a recess of the locking plate 11. The locking member 12 is biased by spring 13 against the locking plate 11.

When the locking member 12 has engaged the locking plate 11, the drive shaft is locked and the stop facility has to be reset by the controller 8 to continue an infusion. Only after the stop facility has been reset, further pumping motion is possible.

In the example shown, the controller 8 resets the stop facility by means of an actuator 14, for example a solenoid. In order to reset the stop facility, the actuator 14 moves the locking member 12 out of its engagement position in which it protrudes into the recess of the locking plate 11.

If the locking plate 11 has only one recess and the stop facility comprises only one locking member 12, such a resetting is required every full turn of the drive shaft 7. However, it is also possible to use several locking members 12 and/or several recesses such that a recess is engaged by a locking member 12 more often. In the example shown, two locking members 12 which alternately block pump motion are arranged opposite each other such that the stop facility has to be reset every half turn of the drive shaft 7.

In the example shown, there is only one recess to be engaged by the locking members 12. However, it is also possible to use a plurality of locking elements, e.g. recesses of a locking plate. Then the stop facility has to be reset more often. If two locking members 12 are to be used alternately, the locking elements, e.g. recesses, should be arranged in such a way that the locking members 12 cannot engage at the same time.

Both locking members 12 are reset by the same actuator 14. Resetting the stop facility by moving one of the locking members 12 to disengage from positive locking engagement activates at least one other locking member 12 so that it will block pump motion after a preset period which is in the example shown a half turn of the locking plate. Activation of a locking member 12 is achieved by movement of the actuator 14 which by moving to disengage one locking member 12 frees the other so that it can engage a rotating locking element, which is in the example shown a recess of the locking plate 11.

When the stop facility stops the pump 1 by locking the drive shaft 7 it also causes a disconnection of the drive motor 5 to avoid unnecessary power consumption. Disconnection of the drive motor 5 may be achieved by a switch which may be actuated by movement of the locking member 12, for example. Preferably, such a switch is temporally delayed after locking of the pump 1 to ensure that the drive motor 7 is only disconnected in case of a failure of the controller 8, i.e. when the stop facility is not reset with a predetermined time, for example a few seconds or less.

FIG. 2 shows schematically another embodiment of an ambulatory infusion device. This device also comprises a rotary peristaltic pump 1 which is driven via a drive shaft 7 by a DC-Motor 5 controlled by a controller 8. The infusion devices shown in FIGS. 1 and 2 differ with respect to the stop facility for stopping the pump by mechanically blocking pump motion.

The stop facility of the device shown in FIG. 2 comprises a reversing transmission 15 which connects the motor 5 to the drive shaft 7. The reversing transmission comprises two parallel shafts 21, 22 which rotate in opposite directions. The shafts are driven by the motor 5 via a gear wheel 23 which meshes with gear wheel 24 fixed to shaft 21 and gear wheel 25 fixed to shaft 22. Gear wheels 24 and 25 are arranged on opposite sides of gear wheel 23 such that they rotate in opposite directions.

A ratchet and pawl mechanism 26a is fixed to shafts 21. The ratchet and pawl mechanism 26a interacts with a gear wheel 27 which can turn relative to shaft 21. When the shaft 21 rotates in a first direction, e.g. clockwise in the example shown, the ratchet and pawl mechanism 26a causes the gear wheel 27 to rotate with the shaft 21. However, rotation of the shaft 21 in opposite direction, e.g. counter clockwise, is not transmitted to the gear wheel 27.

Likewise, ratchet and pawl mechanism 26b interacts with a gear wheel 28 which can turn relative to shaft 22. However, the ratchet and pawl mechanisms 26a and 26b are active in opposite direction. Hence, in the example show the ratchet and pawl mechanism 26b transmits counter-clockwise rotation of the shaft 22 to the gear wheel 28, whereas clockwise rotation of the shaft 22 is not transmitted to the gear wheel 28.

As the gear wheel 27 meshes with gear wheel 28 which in turn meshes with gear wheel 29 fixed to the drive shaft, the ratchet and pawl mechanisms 26a, 26b ensure that gear wheel 29 and therefore the drive shaft 7 always rotate in the same direction regardless of the directions of rotation of shafts 21, 22 and gear wheel 23.

The reversing transmission drives the drive shaft 7 always in the same direction. Hence, resetting of the stop facility by reversing rotation causes the drive shaft to continue to turn and thereby to pump liquid through the tube 2 in the direction of the arrows shown.

As can be seen in FIG. 2, gear wheel 24 of the reversing transmission 15 has a locking structure, for example a groove 17, which is engaged by a pin 18. During an infusion the pin 18 moves along the locking structure 17 until it reaches a limit stop, in the example shown an end of the groove 17, which acts as a locking member. Once this happens, an infusion is stopped as further pump action, i.e. further rotation of the gear wheel 24 in the same direction, is blocked by the pin 18 engaging the limit stop.

To continue an infusion, the controller 8 has to reset the locking mechanism which in the example shown is done by reversing the direction of rotation of the motor 5. Reversing rotation causes the pin 18 to move back along the locking structure 17 until it reaches the limit stop at the other end of the groove. Then the motor 5 has to change direction of rotation again.

The reversing transmission 15 drives the drive shaft 7 always in the same direction. Hence, resetting of the stop facility by reversing rotation causes the drive shaft to continue to turn and thereby to pump liquid through the tube 2 in the direction of the arrows shown.

Thus, embodiments of the infusion device are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. An infusion device having safeguards for protecting a patient from inappropriate infusion during malfunction of an electronic controller, comprising:
    a pump;
    a transmission coupled to the pump;
    a motor coupled to the transmission to operate the pump;
    an electronic controller for automatically controlling the motor; and,
    a mechanical stop facility for stopping the pump by mechanically blocking the transmission from operating the pump when the motor is drivingly coupled to the pump, the mechanical blocking comprising mechanically blocking operating motion of the pump to thereby prevent the pump from generating fluid pressure and also thereby stop continued delivery of an infusion,
    wherein the mechanical stop facility during operation periodically requires resetting by the electronic controller to continue the infusion and thereby limits the amount of potential overdosing and wherein the mechanical stop facility comprises at least two locking members which alternatively block pump motion, and wherein the mechanical stop facility is reset by moving one of the locking members to disengage from positive locking engagement, which activates at least one other locking member so that the other locking member will block pump motion after a preset period.

2. The infusion device in claim 1 wherein the pump is a peristaltic pump.

3. The infusion device in claim 1 wherein the mechanical stop facility comprises an actuator, preferably a solenoid, for resetting the stop facility by moving at least one of the locking members.

4. The infusion device in claim 1 wherein at least one of the locking members is spring biased which blocks pump motion by positive locking.

5. The infusion device in claim 1 wherein the mechanical stop facility blocks pump motion by locking a driveshaft of the pump.

6. The infusion device as in claim 1 wherein the mechanical stop facility comprises a locking plate.

7. The infusion device as in claim 1 wherein the mechanical stop facility comprises a reversing transmission and is reset by reversing direction of rotation.

8. The infusion device as in claim 1 further comprising, a pump motor coupled to the pump wherein the motor is a DC motor.

9. An infusion device having safeguards for protecting a patient from inappropriate infusion during malfunction of an electronic controller, comprising:
    a peristaltic pump;
    a transmission coupled to the peristaltic pump;
    a motor coupled to the transmission to operate the peristaltic pump;
    an electronic controller for automatically controlling the motor; and,
    means for stopping the peristaltic pump by mechanically blocking the transmission from operating the peristaltic pump when the motor is drivingly coupled to the pump and when the means for stopping has not been reset by the electronic controller, the mechanical blocking comprising a positive locking engagement of the transmission with the means for stopping to thereby block operating motion of the pump and thereby prevent the pump from generating fluid pressure and also thereby stop continued delivery of an infusion by the pump; the means for stopping periodically requiring resetting by the electronic controller during operation to disengage the positive locking engagement of the means for stopping and thereby continue the infusion whereby the amount of potential overdosing is limited.

10. A method for safeguarding an infusion device from excessive infusion during a malfunction, comprising:
    resetting a stop facility by an electronic controller for a time interval to prevent the stop facility from blocking a transmission from operating a peristaltic pump, the stop facility operably disposed between a motor and the pump and comprising a first locking member and a second locking member, the second locking member being drivingly coupled to the motor;
    supplying power to the peristaltic pump through the electronic controller to operate the peristaltic pump;
    continuing to supply power to the peristaltic pump after failure in the electronic controller to cease supplying power to the peristaltic pump; and,
    failing to reset the stop facility by failure in the electronic controller to prevent the stop facility from blocking motion of the peristaltic pump; and,
    engaging the first and second locking members of the stop facility to stop the peristaltic pump by mechanically blocking operating motion of the peristaltic pump and thereby preventing the pump from generating fluid pressure during a failure in the electronic controller that continues to supply power to operate the peristaltic pump when not intended by the electronic controller.

11. The method in claim 10 wherein the stop facility comprises at least one blocking member which blocks pump motion by positive locking.

12. The method in claim 10 wherein the stop facility comprises a spring biased locking member.

13. The method in claim 10 wherein the stop facility comprises a reversing transmission having two limit stops that periodically require a reversing of rotation of the reversing transmission.

14. The method in claim 10 wherein the time interval is selected to limit infusion during failure of the electronic controller to control the maximum amount of unintended infusion.

* * * * *